United States Patent
Lu et al.

(10) Patent No.: US 10,300,160 B2
(45) Date of Patent: May 28, 2019

(54) PLASMA LIQUID GENERATING DEVICE

(71) Applicant: Amsalp Biomedical Co., Ltd, Taipei (TW)

(72) Inventors: Jen-Chieh Lu, New Taipei (TW); Yin-Lin Lu, Kaohsiung (TW)

(73) Assignee: AMSALP BIOMEDICAL CO., LTD, Taipei (TW)

( * ) Notice: Subject to any disclaimer, the term of this patent is extended or adjusted under 35 U.S.C. 154(b) by 162 days.

(21) Appl. No.: 15/615,428

(22) Filed: Jun. 6, 2017

(65) Prior Publication Data

US 2017/0348447 A1  Dec. 7, 2017

(30) Foreign Application Priority Data

Jun. 6, 2016  (TW) .............................. 105117874 A (51) Int. Cl.
  *A61L 2/14*  (2006.01)
  *H01J 37/32*  (2006.01)
  *H05H 1/24*  (2006.01)

(52) U.S. Cl.
  CPC .......... *A61L 2/14* (2013.01); *H01J 37/32825* (2013.01); *H05H 1/24* (2013.01); *H05H 1/2406* (2013.01)

(58) Field of Classification Search
  CPC .......... A61L 2/14; H05H 1/2406; H05H 1/24; H05H 1/42; H05H 2245/123; H01J 37/32825; H01J 37/3244; H01J 37/32018; H01J 37/32027; H01J 2237/3321; C23C 16/513; C23C 16/00; C23C 16/0272; C23C 16/26; C23C 16/45565; C23C 16/45578; C23C 16/4558; C23C 16/4585; C23C 16/4586; C23C 16/503; C23C 16/52; C23F 1/08

See application file for complete search history.

(56) References Cited

U.S. PATENT DOCUMENTS

| | | | |
|---|---|---|---|
| 5,413,759 A * | 5/1995 | Campbell | A61L 2/14 422/22 |
| 7,511,246 B2 * | 3/2009 | Morrisroe | G01N 21/73 219/121.48 |
| 2010/0130911 A1 * | 5/2010 | Morfill | H05H 1/24 604/20 |
| 2011/0100556 A1 * | 5/2011 | Liu | C23C 16/513 156/345.43 |

\* cited by examiner

*Primary Examiner* — Walter D. Griffin
*Assistant Examiner* — Cameron J Allen
(74) *Attorney, Agent, or Firm* — Muncy, Geissler, Olds & Lowe, P.C.

(57) ABSTRACT

A plasma liquid generating device includes a tube, a plasma generating module, a flow limiting unit, and a position limiting member. The tube has at least an air inlet and a flow channel outlet. The plasma generating module is disposed adjacent to the air inlet and configured to generate plasma. The flow limiting unit is detachably disposed in the tube, and a distance between the flow limiting unit and the flow channel outlet is greater than a distance between the air inlet and the flow channel outlet. The position limiting member is detachably disposed at the flow channel outlet to limit the position of the flow limiting unit.

16 Claims, 10 Drawing Sheets

PLASMA LIQUID GENERATING DEVICE

CROSS REFERENCE TO RELATED APPLICATIONS

This Non-provisional application claims priority under 35 U.S.C. § 119(a) on Patent Application No(s). 105117874 filed in Taiwan, Republic of China on Jun. 6, 2016, the entire contents of which are hereby incorporated by reference.

BACKGROUND OF THE INVENTION

Field of Invention

The present disclosure relates to a plasma liquid generating device and, in particular, to a plasma liquid generating device that can utilize the pressure difference caused by water flow so as to suck air into the tube.

Related Art

As the progress of technology, the requirements for high quality life are desired. Many researches indicate that the small amount of plasma can be resolved in water for providing the sterilization function. Accordingly, it is benefit to utilize the plasma water to clean foods, dishes or human bodies.

However, the device for generating the plasma water is usually activated by electricity for generating plasma. Thus, the installation of the device includes many limitations. For example, the places for installing the device for generating the plasma water (e.g. kitchen or bathroom) usually have insufficient sockets, and the installation of the device is limited by the location of the available socket.

Besides, for example, many people have more concerns about the water for taking a bath. For example, it is possible to add hot spring tablets or powder into water for bathing. However, the hot spring tablets or powder must be added into the bathtub and require a lot of water. Thus, it is not convenient and not economic. In addition, there is also a need for additive in the water.

SUMMARY OF THE INVENTION

In one embodiment, a plasma liquid generating device, which includes a tube, a plasma generating module, a flow limiting unit, and a position limiting member. The tube has at least an air inlet and a flow channel outlet. The plasma generating module is disposed adjacent to the air inlet and configured to generate plasma. The flow limiting unit is detachably disposed in the tube, and a distance between the flow limiting unit and the flow channel outlet is greater than a distance between the air inlet and the flow channel outlet. The position limiting member is detachably disposed at the flow channel outlet to limit a position of the flow limiting unit.

In one embodiment, the plasma generating module ionizes air outside the tube to form the plasma, a water flow passes through the flow limiting unit so as to suck the plasma into the tube through the air inlet, and the plasma is then mixed in the water flow.

In one embodiment, the flow limiting unit has a ball shape, and a surface of the flow limiting unit contains soluble minerals.

In one embodiment, the flow limiting unit includes a core part and a functional coating part covering the core part. The core part includes a non-water soluble material, and the functional coating part includes a water soluble material.

In one embodiment, the functional coating part includes a functional surface layer and a deep layer disposed between the core part and the functional surface layer. The functional surface layer includes soluble minerals, and the deep layer has a water soluble property different from the functional surface layer.

In one embodiment, the flow channel outlet of the tube is large enough for configuring the flow limiting unit.

In one embodiment, the plasma liquid generating device further includes a covering body disposed at one end of the tube. The position limiting member is disposed on the covering body and extends toward an inside part of the tube. When the flow limiting unit is pushed by a water flow, the position limiting member stops the flow limiting unit to prevent the water flow to carry the flow limiting unit toward the flow channel outlet.

In one embodiment, the covering body and the tube are connected by screwing, locking or a fixing member.

In one embodiment, the position limiting member includes a ring body and at least a position limiting stick. The ring body has one side matching the flow channel outlet. The position limiting stick extends from the ring body toward an inside part of the tube. When a water flow pushes the flow limiting unit, the position limiting stick stops the flow limiting unit to prevent the water flow to carry the flow limiting unit.

In one embodiment, the plasma liquid generating device further includes a driving circuit and an adjust-controlling unit. The driving circuit is coupled with the plasma generating module and drives the plasma generating module to generate first type plasma particles and second type plasma particles. The adjust-controlling unit is coupled with the driving circuit and controls the driving circuit to control a generation proportion of the first type plasma particles and the second type plasma particles generated by the plasma generating module.

In one embodiment, the first type plasma particles are ozone, and the second type plasma particles are nitrate ions.

In one embodiment, the driving circuit outputs a driving voltage to the plasma generating module. When the driving voltage has a high frequency, the generated nitrate ions are more than the generated ozone in the generation proportion. When the driving voltage has a low frequency, the generated ozone is more than the generated nitrate ions in the generation proportion.

In one embodiment, the adjust-controlling module includes a controller such as a touch screen or a knob.

In one embodiment, the plasma liquid generating device is cooperated with a water output device, and the water output device is a showerhead or a faucet.

In one embodiment, the plasma liquid generating device further includes a hydroelectric generator for providing power to the plasma generating module.

In one embodiment, the plasma liquid generating device further includes a waterproof housing for accommodating the tube, the plasma generating module, the flow limiting unit, the position limiting member, and the hydroelectric generator.

In one embodiment, the plasma generating module includes at least a plasma generator, such as an atmospheric-pressure plasma generator. The atmospheric-pressure plasma generator is, for example, a dielectric barrier discharge (DBD) plasma generator.

In one embodiment, the plasma liquid generating device includes a plurality of plasma generating modules. The tube has a plurality of air inlets, and the plasma generating modules are disposed corresponding to the air inlets.

In one embodiment, a plasma liquid generating device, which includes a tube, a plasma generating module, a flow limiting unit, a position limiting member, a hydroelectric generator, a driving circuit, a waterproof housing, and an adjust-controlling unit. The tube has at least an air inlet and a flow channel outlet. The plasma generating module is disposed adjacent to the air inlet and configured to ionize air outside the tube to form plasma. The flow limiting unit is detachably disposed in the tube, and a distance between the flow limiting unit and the flow channel outlet is greater than a distance between the air inlet and the flow channel outlet. A water flow passes through the flow limiting unit so as to suck the plasma into the tube through the air inlet, and the plasma is then mixed in the water flow. The flow channel outlet of the tube is large enough for configuring the flow limiting unit. The position limiting member is detachably disposed at the flow channel outlet to limit a position of the flow limiting unit. The hydroelectric generator is configured for providing power to the plasma generating module. The driving circuit is coupled with the plasma generating module and drives the plasma generating module to generate ozone and nitrate ions. The waterproof housing is configured for accommodating the tube, the plasma generating module, the flow limiting unit, the position limiting member, the driving circuit, and the hydroelectric generator. The adjust-controlling unit is coupled with the driving circuit and controls the driving circuit to control a generation proportion of the ozone and the nitrate ions generated by the plasma generating module. The driving circuit outputs a driving voltage to the plasma generating module. When the driving voltage has a high frequency, the generated nitrate ions are more than the generated ozone in the generation proportion. When the driving voltage has a low frequency, the generated ozone is more than the generated nitrate ions in the generation proportion.

In one embodiment, the flow limiting unit has a ball shape, and a surface of the flow limiting unit contains soluble minerals.

In one embodiment, the flow limiting unit includes a core part and a functional coating part covering the core part. The core part includes a non-water soluble material, and the functional coating part includes a water soluble material.

In one embodiment, the functional coating part includes a functional surface layer and a deep layer disposed between the core part and the functional surface layer. The functional surface layer includes soluble minerals, and the deep layer has a water soluble property different from the functional surface layer.

In one embodiment, the plasma liquid generating device further includes a covering body disposed at one end of the tube. The position limiting member is disposed on the covering body and extends toward an inside part of the tube. When the flow limiting unit is pushed by the water flow, the position limiting member stops the flow limiting unit to prevent the water flow to carry the flow limiting unit toward the flow channel outlet.

In one embodiment, the covering body and the tube are connected by screwing, locking or a fixing member.

In one embodiment, the position limiting member includes a ring body and at least a position limiting stick. The ring body has one side matching the flow channel outlet. The position limiting stick extends from the ring body toward an inside part of the tube. When a water flow pushes the flow limiting unit, the position limiting stick stops the flow limiting unit to prevent the water flow to carry the flow limiting unit.

In one embodiment, the adjust-controlling module includes a controller such as a touch screen or a knob.

In one embodiment, the plasma liquid generating device is cooperated with a water output device, and the water output device is a showerhead or a faucet.

In one embodiment, the plasma generating module includes at least a plasma generator, such as an atmospheric-pressure plasma generator. The atmospheric-pressure plasma generator is, for example, a dielectric barrier discharge (DBD) plasma generator.

In one embodiment, the plasma liquid generating device includes a plurality of plasma generating modules. The tube has a plurality of air inlets, and the plasma generating modules are disposed corresponding to the air inlets.

As mentioned above, the flow limiting unit of the plasma liquid generating device is replaceable. In practice, the user can remove the position limiting member from the tube and then take the flow limiting unit out of the tube. Besides, the user can place another flow limiting unit into the plasma liquid generating device based on personal preferences or applications.

In addition, the plasma liquid generating device can be directly driven by the flowing water in the pipe for generating plasma, and the generated plasma can be added into the water in the pipe so as to activate the water. Accordingly, the plasma activated water can be generated for cleaning. Moreover, the hot spring tablet can be directly installed in the pipe through the plasma liquid generating device. Accordingly, the special water (e.g. hot spring water) can be easily provided to the user by showering, and the amount of water for taking a bath can be sufficiently reduced.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The embodiments of the disclosure will be apparent from the following detailed description, which proceeds with reference to the accompanying drawings, wherein the same references relate to the same elements. Moreover, the drawings of all implementation are schematic, and they do not mean the actual size and proportion. The terms of direction recited in the disclosure, for example up, down, left, right, front, or rear, only define the directions according to the accompanying drawings for the convenience of explanation but not for limitation. The names of elements and the wording recited in the disclosure all have ordinary meanings in the art unless otherwise stated. Therefore, a person skilled in the art can unambiguously understand their meanings.

Figure 1:
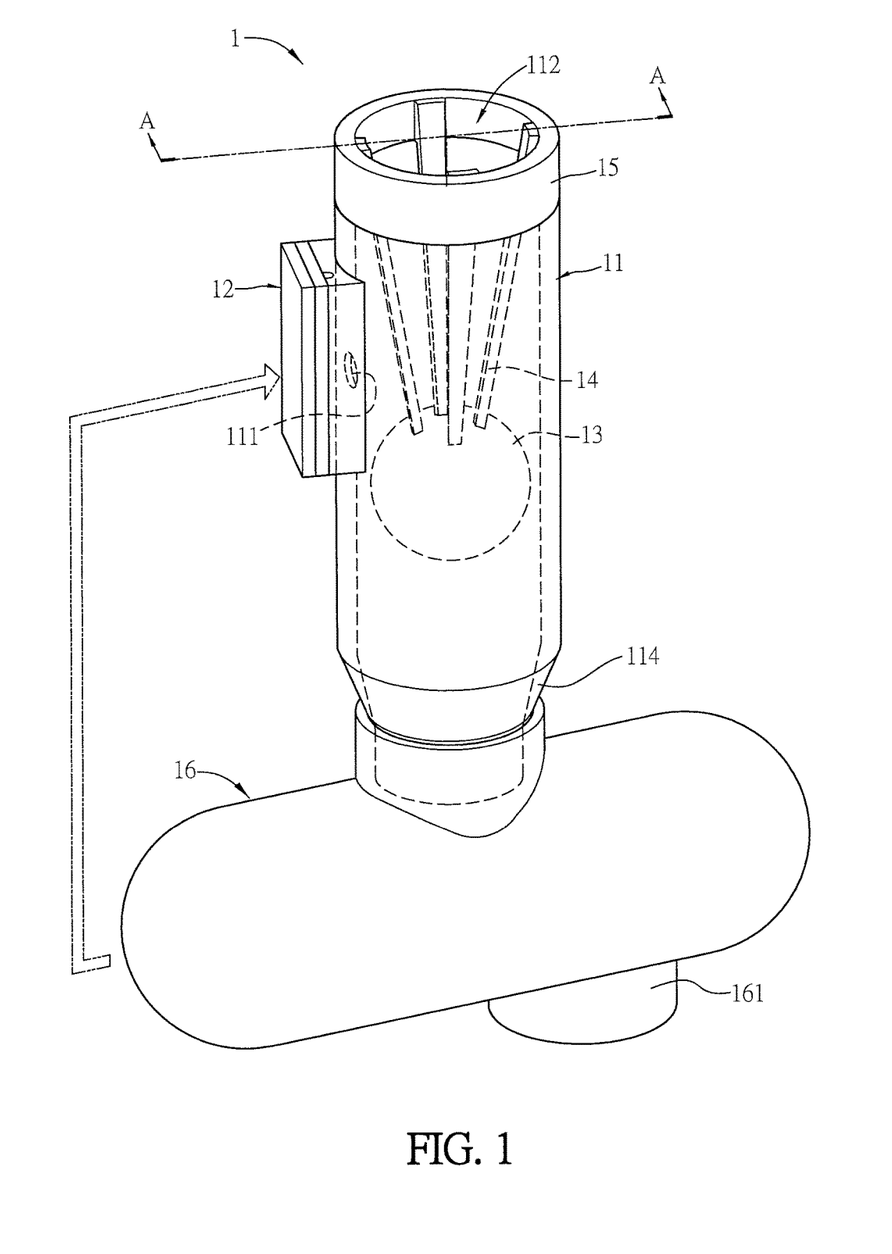
FIG. 1 is a schematic diagram showing a plasma liquid generating device according to an embodiment.
Figure 2:
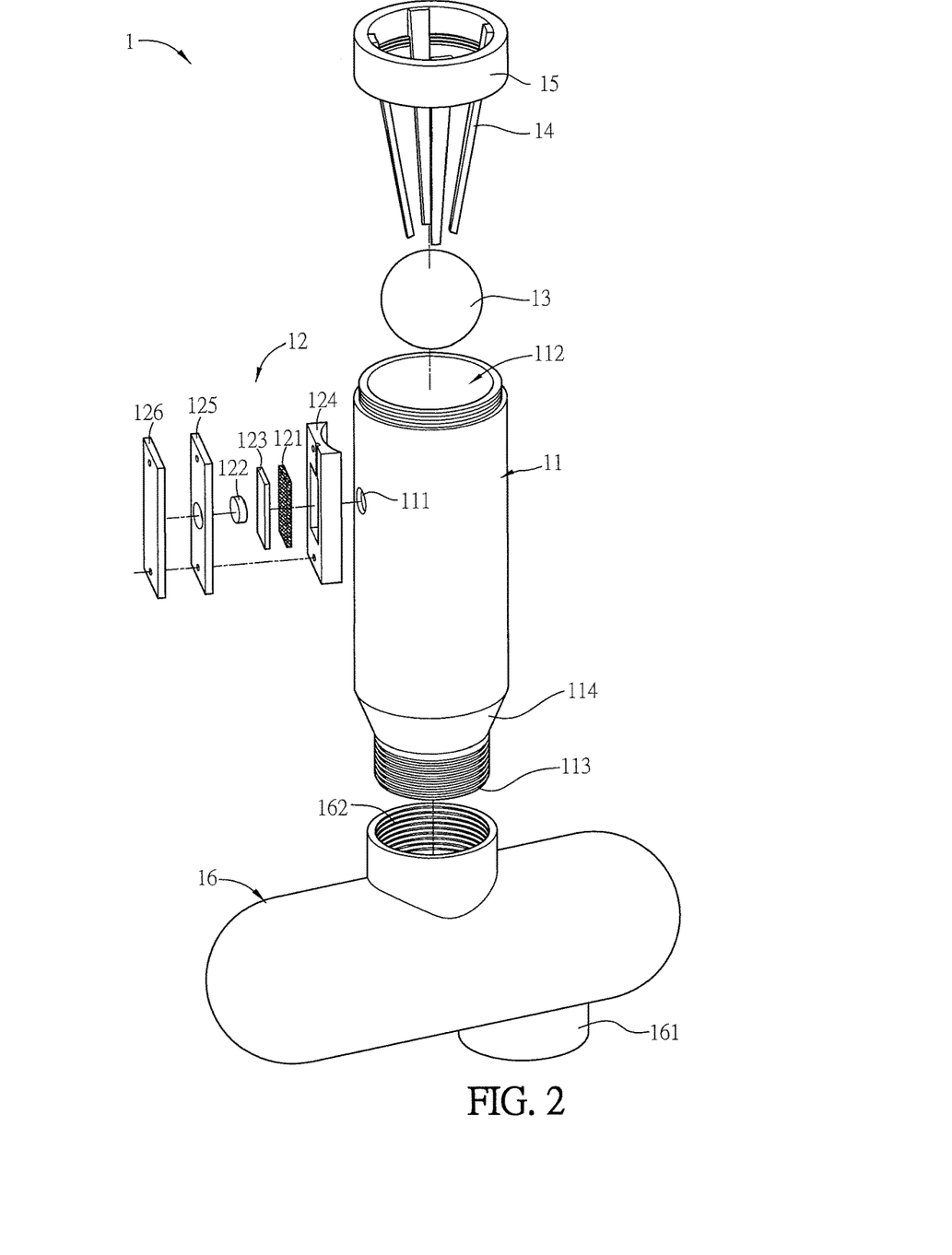
FIG. 2 is an exploded view of the plasma liquid generating device of FIG. 1.
Figure 3:
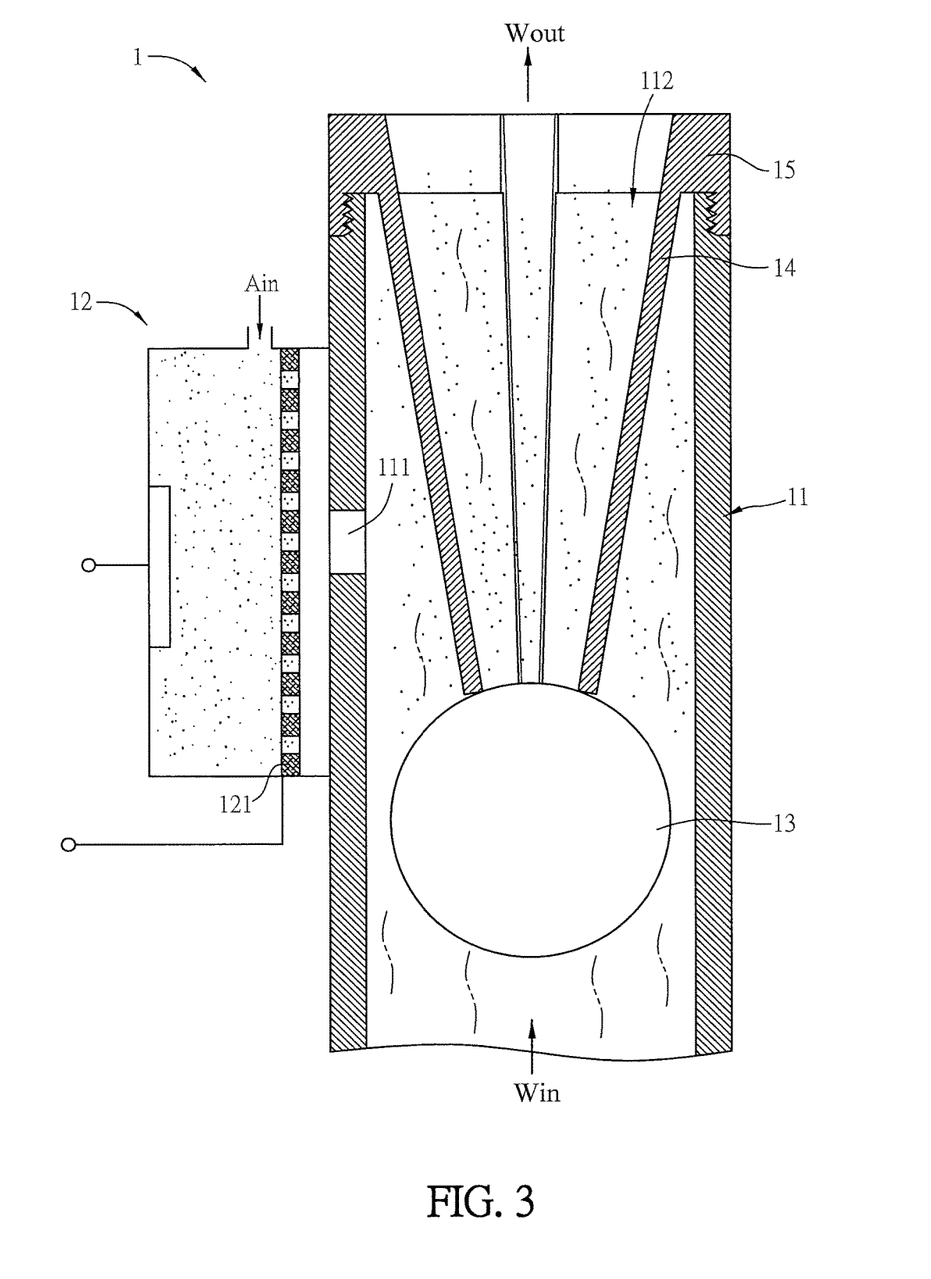
FIG. 3 is a sectional view of the plasma liquid generating device of FIG. 1 along the line A-A.

FIG. 1 is a schematic diagram showing a plasma liquid generating device according to an embodiment, FIG. 2 is an exploded view of the plasma liquid generating device of FIG. 1, and FIG. 3 is a sectional view of the plasma liquid generating device of FIG. 1 along the line A-A. Referring to FIGS. 1 to 3, a plasma liquid generating device 1 can be cooperated with a water output device, such as a showerhead or a faucet. The plasma liquid generating device 1 includes a tube 11, a plasma generating module 12, a flow limiting unit 13, and a position limiting member 14. The tube 11 has at least one air inlet 111 and a flow channel outlet 112. The plasma generating module 12 is disposed adjacent to the air inlet 111 and configured to generate plasma. The flow limiting unit 13 is detachably disposed in the tube 11, and a distance between the flow limiting unit 13 and the flow channel outlet 112 is greater than a distance between the air inlet 111 and the flow channel outlet 112. The position limiting member 14 is detachably disposed at the flow channel outlet 112 to limit a position of the flow limiting unit 13. The plasma generating module 12 can ionize air outside the tube 11 to form the plasma.

The position limiting member 14 is a block member disposed along the water flow direction (toward the flow channel outlet 112). Functionally, the position limiting member 14 can stop the flow limiting unit 13 in front of the flow channel outlet 112, thereby avoiding the flow limiting unit 13 from exiting the flow channel outlet 112. Besides, the position limiting member 14 can limit the flow limiting unit 13 within a specific region along the water flow direction. In more specific, the position limiting member 14 can limit the flow limiting unit 13 behind the air inlet 111. For example, the widest part of the flow limiting unit 13 is not over the air inlet 111, so that the air inlet 111 can input more air and plasma.

In this embodiment, the flow limiting unit 13 has a ball shape (e.g. a ball or an oval ball). Otherwise, the flow limiting unit 13 may have a cylinder shape or other shapes. The tube 11 and the flow limiting unit 13 can form a Venturi tube structure. When the liquid flows through the tube 11 from bottom, the sectional area of the tube 11 are changed (from large to small), so that the flow speed is increased so as to form a negative pressure area (based on Bernoulli's Principle). Accordingly, the plasma generated by the plasma generating module 12 can be sucked into the tube 11 through the air inlet 111. In other aspects, the flow limiting unit 13 can have other shapes with a sectional area changed from large to small for forming the negative pressure area.

In order to form a greater negative pressure for sucking more plasma, the flow limiting unit 13 is preferably disposed adjacent to the air inlet 111, which can make the fluid flow faster around the air inlet 111. This configuration can provide a larger negative pressure to suck more amount of plasma.

In addition, a position limiting portion 114 is configured inside the tube 11 for preventing the flow limiting unit 13 from exiting the flow channel inlet 113. In this embodiment, the position limiting portion 114 is a shrink portion in the tube 11 located close to the flow channel inlet 113. Accordingly, when the flow limiting unit 13 is placed into the tube 11 through the flow channel outlet 112, it can be stopped at the position limiting portion 114. When water flows from the flow channel inlet 113 to the flow channel outlet 112, the position limiting member 14 can prevent the flow limiting unit 13 from exiting the flow channel outlet 112. Thus, the flow limiting unit 13 can be limited by the position limiting member 14 and the position limiting portion 114 between the position limiting portion 114 and the air inlet 111. In other aspects, the position limiting portion 114 can be a bolt or a ring installed inside the tube 11.

As mentioned above, the flow limiting unit 13 is not fixed inside the tube 11. When a water flow passes through the tube 11, the flow limiting unit 13 is pushed back and urged against the position limiting member 14. Since the position limiting member 14 is fixed to the tube 11, it can stop the flow limiting unit 13 and limit the flow limiting unit 13 around the air inlet 111. When no water flow is applied to the tube 11, the flow limiting unit 13 is not pushed to the position limiting member 14. Thus, the flow limiting unit 13 will be held by the position limiting portion 114 so as to prevent it from falling through the water inlet.

In this embodiment, the plasma liquid generating device 1 further includes a covering body 15 and a hydroelectric generator 16. The hydroelectric generator 16 can provide electric power to the plasma generating module 12. The water flow enters the hydroelectric generator 16 through the inlet 161 and exits the hydroelectric generator 16 through the outlet 162. After leaving the hydroelectric generator 16, the water flow enters the tube 11. Before being mixed with the plasma particles, the water flow flows through the hydroelectric generator 16 so as to enable the hydroelectric generator 16 to output the supply voltage. The covering body 15 is connected with one end of the tube 11. For example, the covering body 15 is connected with the tube 11 at the flow channel outlet 112 by screwing. Of course, the covering body 15 can also be connected with the tube 11 at the flow channel outlet 112 by locking or by a fixing member. The position limiting member 14 is disposed on the covering body 15. For example, the position limiting member 14 can be screwed or inserted on the covering body 15. Otherwise, the position limiting member 14 and the covering body 15 can be integrated as one piece.

When the flow limiting unit 13 is pushed by the water flow, the position limiting member 14 can stop the flow limiting unit 13 so as to fix the flow limiting unit 13 within the range of the position limiting member 14. Accordingly, the position of the flow limiting unit 13 can be restricted with a range, which is determined by the length of the position limiting member 14. In one embodiment, the narrowest part of tube 11 caused by the flow limiting unit 13 is corresponding to the air inlet 111. To be noted, the skilled person can make any modification without departing the spirit of the invention, and these modifications are within the scope of the invention. For example, the shape, size or position of the position limiting member 14 can be properly modified, and any modified position limiting member 14 that can restrict the position of the flow limiting unit 13 is within the scope of the invention.

The flow limiting unit 13 is replaceable. In practice, the user can remove the position limiting member 14 from the tube 11 and then take the flow limiting unit 13 out of the tube 11 through the flow channel outlet 112. The size of the flow limiting unit 13 is smaller than the diameter of the tube 11, so that the flow limiting unit 13 can be easily placed into or taken out of the tube 11 through the flow channel outlet 112.

In one aspect, the surface of the flow limiting unit 13 contains soluble minerals, such as the minerals prepared by purifying the hot spring mud. When the liquid flows through the flow limiting unit 13, some minerals attached on the surface of the flow limiting unit 13 are dissolved in the fluid, so that the outputted fluid is similar to the hot spring water. Accordingly, the user can easily enjoy the hot spring water. For example, if the plasma liquid generating device 1 is cooperated with a showerhead, the user can take a shower with the hot spring water. This approach allows the user to enjoy the hot spring water without a bathtub, and sufficiently reduces the amount of water for taking a bath. Moreover, when the minerals attached on the surface of the flow limiting unit 13 is running out, it is possible to detach the position limiting member 14 to open the plasma liquid generating device 1 for replacing the flow limiting unit 13. In addition, the used flow limiting unit 13 can be recycled and reattaching new soluble minerals.

In addition, the plasma generating module 12 is, for example, a DBD (dielectric barrier discharge) plasma generator, which includes electrodes 121 and 122, an insulation member 123, electrode fixing members 124 and 125, and a plastic member 126. The electrodes 121 and 122 are disposed in the slots of the electrode fixing members 124 and 125, respectively. The insulation member 123 is installed between the electrode fixing members 124 and 125 (between the electrodes 121 and 122). The plastic member 126 is installed outside of the electrode fixing member 125. The electrode fixing members 124 and 125 and the plastic member 126 can be assembled by screwing. The air inlet 111 can be disposed on the electrode fixing member 124. In practice, the air inlet 111 can be a slot formed on the electrode fixing member 124.

The electrode fixing member 124 is installed outside the tube 11, and the air inlet 111 of the tube 11 is aligned to the electrode 121. The electrode 121 is made of, for example, stainless steel mesh, and the electrodes 121 and 122 are electrically connected to the power source for generating plasma. The generated plasma enters the tube 11 through the stainless steel mesh and the air inlet 111. For example, the electrodes 121 and 122 are connected to the power source or a driving circuit by wires.

Figure 4A:
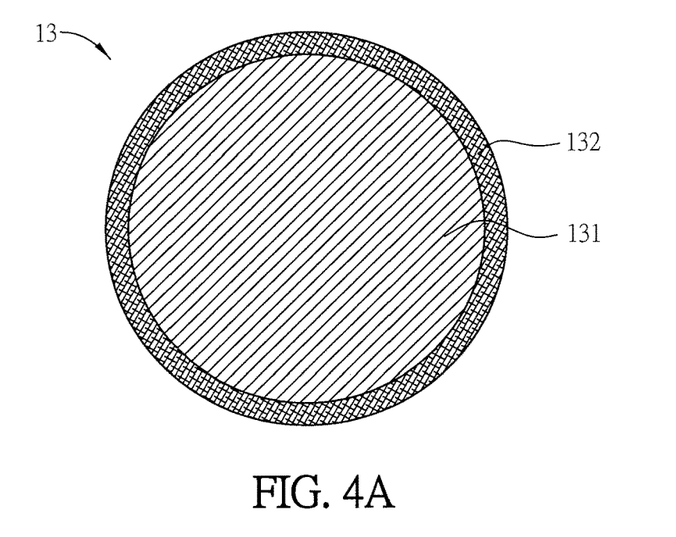
FIGS. 4A and 4B are schematic diagrams showing the flow limiting unit of FIG. 1.

FIGS. 4A and 4B are schematic diagrams showing the flow limiting unit of FIG. 1. As shown in FIG. 4A, the flow limiting unit 13 includes a core part 131 and a functional coating part 132 covering the core part 131. The core part 131 includes a non-water soluble material, and the functional coating part 132 includes a water soluble material. The functional coating part 132 may include the soluble minerals as mentioned above. When the functional coating part 132 (the soluble minerals) is running out, the flow limiting unit 13 may only remain the core part 131 and the water outputted by the plasma generating device 1 only outputs the normal water without the above mentioned functional feature. In this case, the user can take the covering body 15 and the position limiting member 14 off the tube 11, and then remove the flow limiting unit 13. Afterwards, the user may put a new flow limiting unit 13 with the functional coating part 132 into the tube 11, and then install the covering body 15 and the position limiting member 14.

Figure 4B:
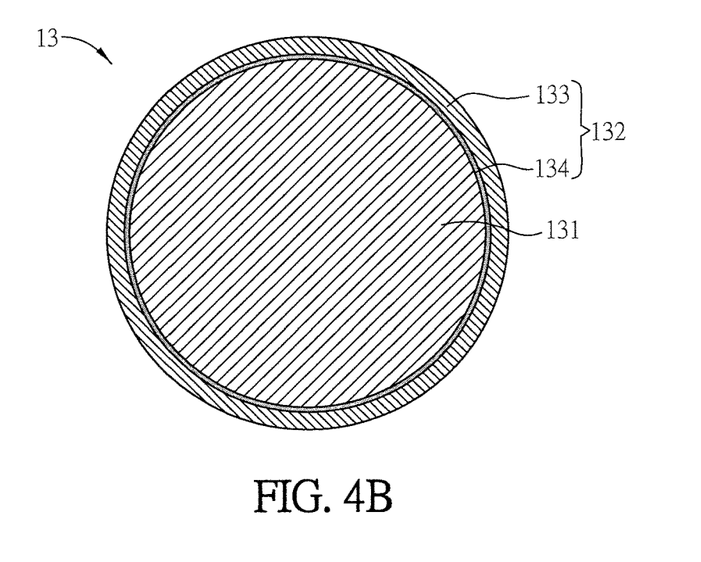

As shown in FIG. 4B, the flow limiting unit 13 includes a core part 131 and a functional coating part 132 covering the core part 131. The core part 131 includes a non-water soluble material, and the functional coating part 132 includes a water soluble material. The functional coating part 132 includes a functional surface layer 133 and a deep layer 134 disposed between the core part 131 and the functional surface layer 133. The functional surface layer 133 is thicker than the deep layer 134. The functional surface layer 133 includes soluble minerals as mentioned above, and the deep layer 134 has a water soluble property different from the functional surface layer 134. For example, when the deep layer 134 is dissolved into water, it may generate a color, a touch feeling, or an amount of bubbles that is different from that generated by dissolving the functional surface layer 133. In general, the functional surface layer 133 is running out earlier than the deep layer 134, so that the different feature of the deep layer 134 can be used to remind the user that the functional surface layer 133 has run out.

Figure 5A:
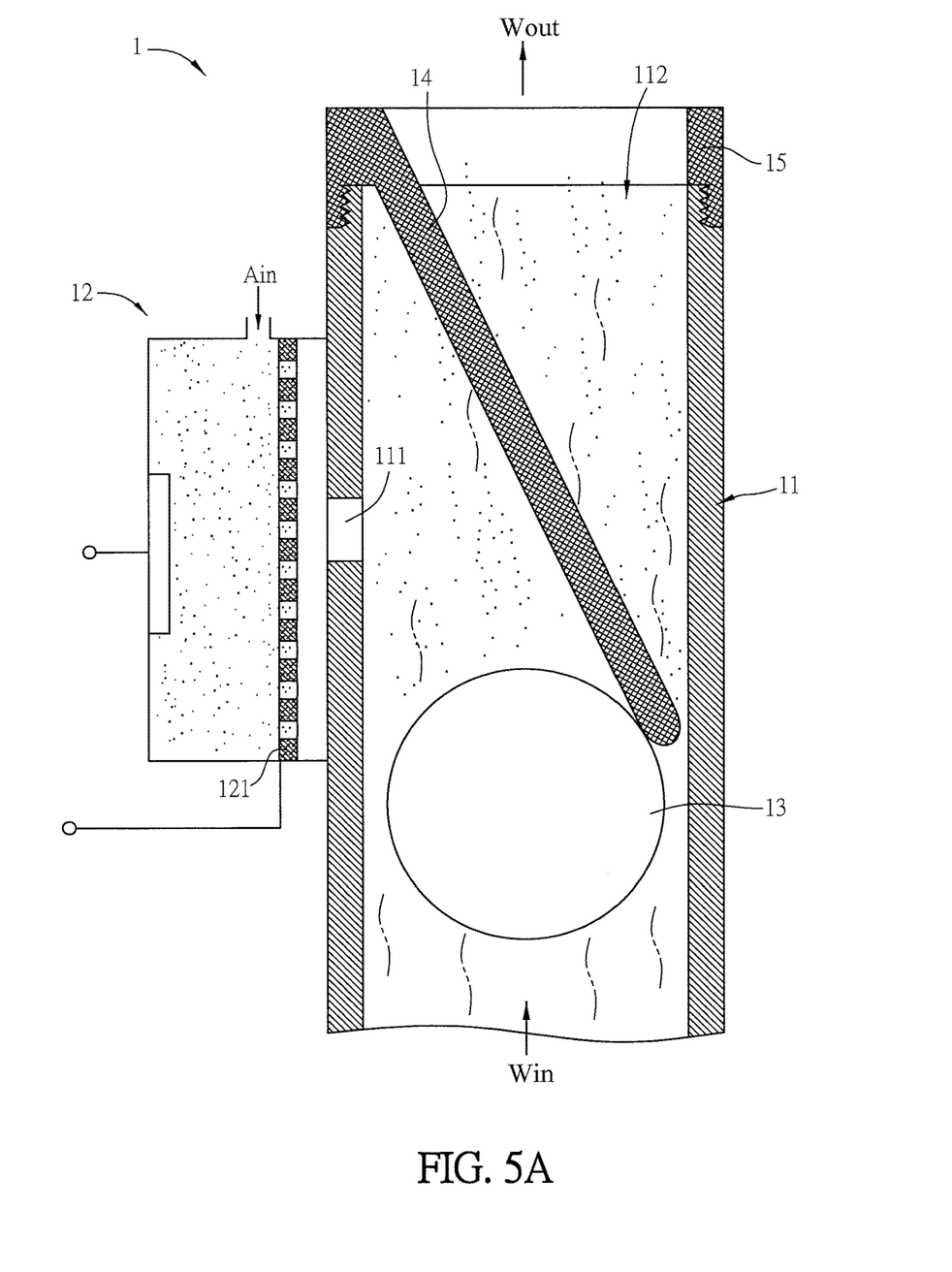
FIGS. 5A and 5B are schematic diagrams showing different aspects of the position limiting member of FIG. 1.
Figure 5B:
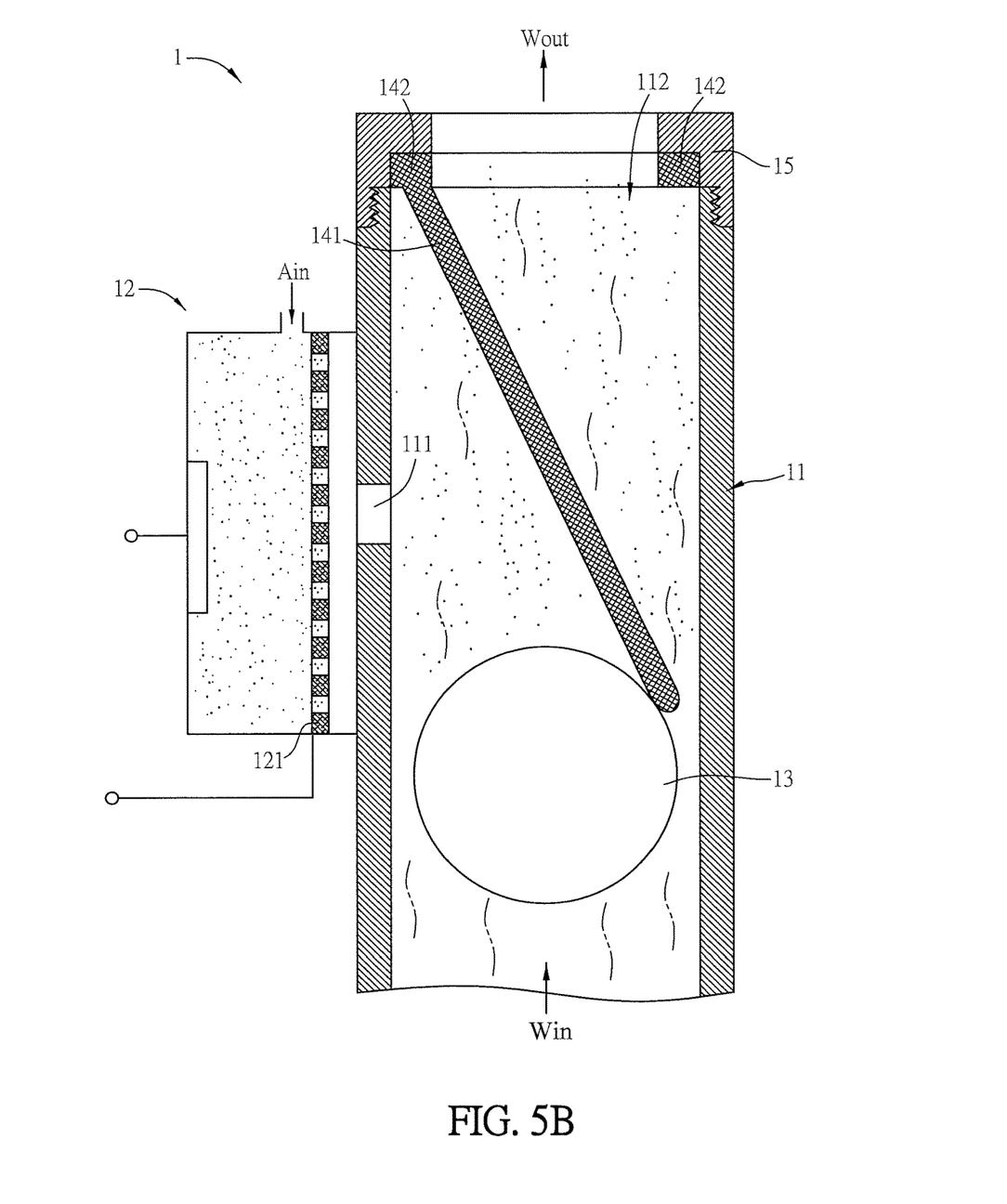

FIGS. 5A and 5B are schematic diagrams showing different aspects of the position limiting member of FIG. 1.

Different from the aspect shown in FIG. 3, the plasma liquid generating device 1 of FIG. 5A includes only one position limiting member 14. As shown in FIG. 5B, the position limiting member 14 includes a ring body 141 and one or more position limiting stick 142. In this case, the position limiting member 14 includes one position limiting stick 142. The position limiting member 14 is entirely disposed in the tube 11, and the ring body 141 has one side matching the flow channel outlet 112. The top of the ring body 141 is covered by the covering body 15 so as to prevent the position limiting member 14 from falling out through the flow channel outlet 112. The position limiting stick 142 extends from the ring body 141 toward an inside part of the tube 11. In this embodiment, the ring body 141 and the position limiting stick 142 are integrally formed as one piece. When the water flow pushes the flow limiting unit 13, the position limiting stick 142 stops the flow limiting unit 13 to prevent the water flow to carry the flow limiting unit 13. Accordingly, the flow limiting unit 13 can be restricted within the range of the position limiting stick 142. In other words, the position range of the flow limiting unit 13 can be determined according to the length of the position limiting stick 142. In one embodiment, the narrowest part of tube 11 caused by the flow limiting unit 13 is preferably corresponding to the air inlet 111. To be noted, the skilled person can make any modification without departing the spirit of the invention, and these modifications are within the scope of the invention. For example, the shape, size or position of the position limiting stick 142 can be properly modified, and any modified position limiting stick 142 that can restrict the position of the flow limiting unit 13 is within the scope of the invention.

Besides, the position limiting member 14 can float along with the flow limiting unit 13, and the position limiting member 14 is located between the flow limiting unit 13 and the covering body 15.

Figure 6:
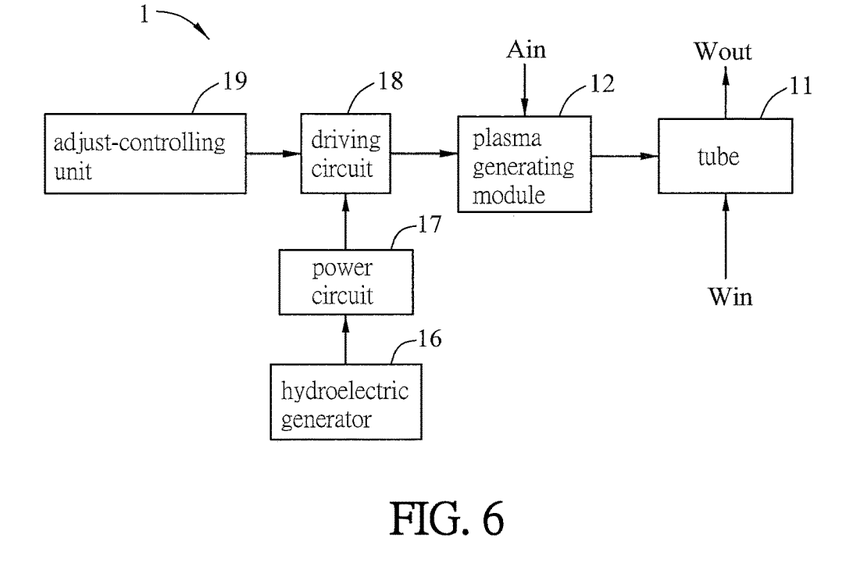
FIG. 6 is a functional block diagram showing the plasma liquid generating device of FIG. 1.
Figure 7:
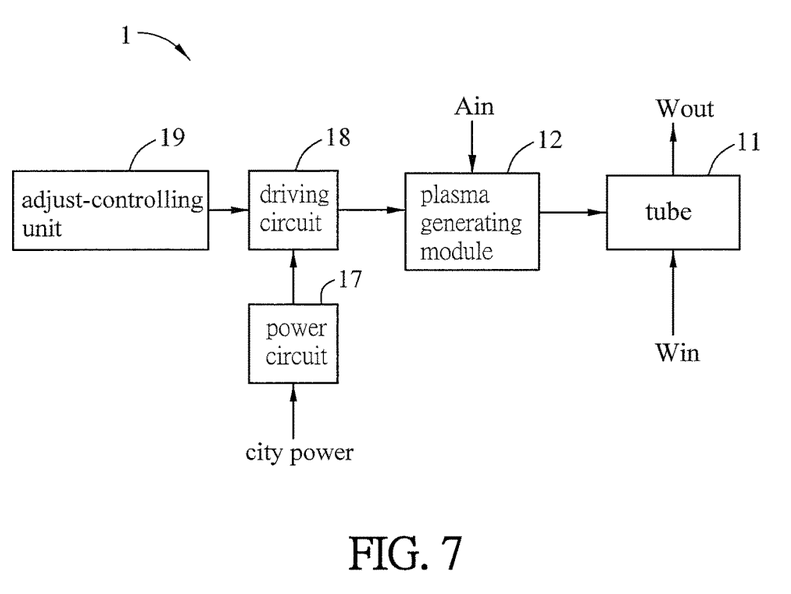
FIG. 7 is a functional block diagram showing a plasma liquid generating device according to another embodiment.

FIG. 6 is a functional block diagram showing the plasma liquid generating device of FIG. 1. The plasma liquid generating device 1 further includes a driving circuit 18, an adjust-controlling unit 19, and a power circuit 17. The plasma generating module 12 includes at least one plasma generator, which can ionize the entered air Ain so as to at least generate first type plasma particles and second type plasma particles. The entered air majorly contains oxygen and nitrogen. The plasma generator can ionize the oxygen and nitrogen so as to generate a plasma containing ozone ($O_3$), nitrate ions ($NO_3^-$), and the likes. To be noted, the first type plasma particles are, for example but not limited to, ozone ($O_3$), and the second type plasma particles are, for example but not limited to, nitrate ions ($NO_3^-$). Ozone ($O_3$) can be utilized for sterilization, and nitrate ions ($NO_3^-$) have slightly acidic for removing the stratum corneum of skin. When the water containing these types of plasma particles (ozone and nitrate ions), it can be used for cleaning skin (face or body washing) so as to provide cosmetic and sterilization functions and can be easily used.

The plasma generating module 12 is carried out based on the atmospheric-pressure plasma technology, which can increase the voltage to thousands volts or more. Accordingly, the electrons in the air can collide for multiple times within a limited space so as to accumulate sufficient electricity for ionizations, thereby generating the desired plasma. The atmospheric-pressure plasma technology can generate plasma under atmospheric pressure without the vacuum chamber and pump applied in the low-pressure plasma generation technology. Thus, the atmospheric-pressure plasma technology is more economic and efficiency, so that it can be applied in the general consumer products.

The plasma generator is, for example, an atmospheric-pressure plasma generator based on the technology of plasma jet, dielectric barrier discharge (DBD), corona discharge, plasma torch, or the likes. In this embodiment, the plasma generator generates the plasma based on, for example but not limited to, the DBD technology. In more details, the DBD technology utilizes high voltage and introduces an isolation plate between the electrodes for stabling the plasma.

The driving circuit 18 is coupled with the plasma generator of the plasma generating module 12 and drives the plasma generator of the plasma generating module 12 to generate the first type plasma particles and the second type plasma particles. The adjust-controlling module 19 is coupled with the driving circuit 18 and controls the driving circuit 18 to adjust a generation proportion of the first type plasma particles and the second type plasma particles generated by the plasma generating module 12. In other words, the user can optionally operate the adjust-controlling module 19 to adjust the settings of the driving signals (e.g. frequency, voltage, intensity or waveform) for adjusting a generation proportion of the first type plasma particles and the second type plasma particles generated by the plasma generating module 12. Accordingly, the proportions of the plasma particles in the plasma liquid can be controlled by the user.

In this embodiment, the first type plasma particles are ozone ($O_3$), and the second type plasma particles are nitrate ions ($NO_3^-$). The plasma generating module 12 can generate the plasma particles of different proportions based on different driving signals. That is, the user can operate the adjust-controlling module 19 to adjust the settings or parameters of the plasma generating module 12, thereby adjusting the generation proportion of the plasma particles. For example, when the user wants to obtain a stronger sterilization function, he/she can operate the adjust-controlling module 19 to increase the proportion of ozone in the plasma particles, thereby mixing more ozone into the plasma liquid. Otherwise, when the user needs a function of removing stratum corneum, he/she can operate the adjust-controlling module 19 to increase the proportion of nitrate ions in the plasma particles, thereby mixing more nitrate ions into the plasma liquid.

In addition, the adjust-controlling module 19 may include a controller such as a touch screen or a knob, and the controller can individually carry out the function of the adjust-controlling module 19. When the controller is a touch screen, the user can directly operate the touch screen to control the adjust-controlling module 19 to output the adjust signal. When the controller is a knob, the user can tune the knob to control the adjust-controlling module 19 to output the adjust signal. Then, the adjust signal is inputted to the driving circuit 18 for adjusting the settings of the driving signal. In addition, the driving circuit 18 can control the plasma generating module 12 according to the adjust signal so as to adjust a generation proportion of the first type plasma particles and the second type plasma particles.

The power circuit 17 can output a supply voltage to the driving circuit 18. The power circuit 17 can output a DC voltage or an AC voltage. Besides, the power circuit 17 may further include a transformer, a frequency converter, a rectifier or an inverter depending on the required voltage. In addition, if the adjust-controlling module 19 includes an electronic component, the power circuit 17 can also output the supply voltage to the adjust-controlling module 19.

In this embodiment, the power circuit 17 is coupled to the hydroelectric generator 16. Before being mixed with the plasma particles, the liquid flows through the hydroelectric generator 16 so as to enable the hydroelectric generator 16 to output the supply voltage V. In more detailed, the water Win enters the hydroelectric generator 16 and pushes the impeller of the hydroelectric generator 16 to generate electricity energy. In practice, the user can easily plug the water pipe to the inlet of the hydroelectric generator 16 and turn on the water valve, and then the water can flow into the hydroelectric generator 16 to enable the hydroelectric generator 16 to output voltage to other house equipment. For example, the hydroelectric generator 16 may output a supply voltage V (e.g. DC 12 Volts and 10 Watts) for driving the driving circuit 18 and the adjust-controlling module 19. In different embodiments, the power circuit 17 may not include the hydroelectric generator 16, but be activated by city power.

Figure 8:
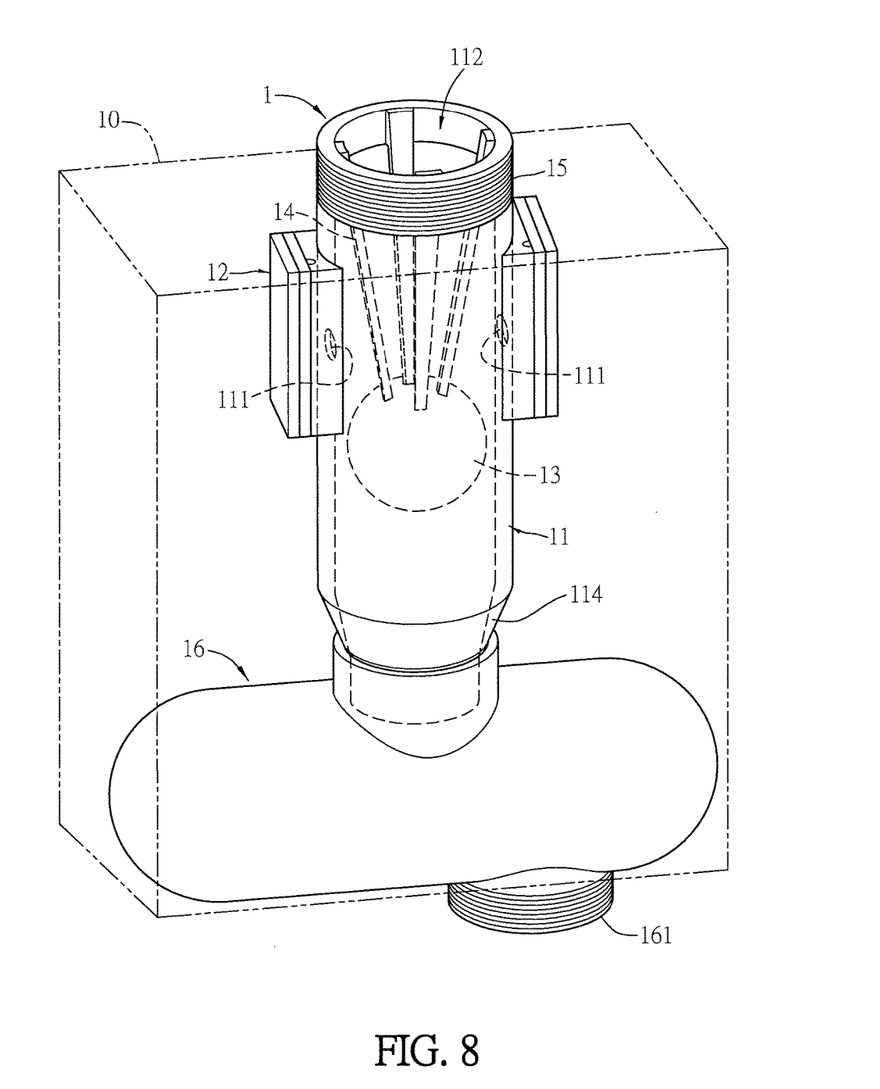
FIG. 8 is a schematic diagram showing a plasma liquid generating device according to another embodiment.

FIG. 8 is a schematic diagram showing a plasma liquid generating device according to another embodiment. As shown in FIG. 8, the plasma liquid generating device 1 further includes a housing 10 for accommodating the tube 11, the plasma generating module 12, the flow limiting unit 13, the position limiting member 14, the body of the hydroelectric generator 16, the power circuit 17 (not shown), and the driving circuit 18 (not shown). Herein, the housing 10 is drawn as dotted lines for easy illustrations. In this case, the housing 10 is a waterproof housing and can be applied to the above embodiments.

The plasma liquid generating device 1 has a compact size and can generate electricity by itself (the external power supply is unnecessary). Thus, the plasma liquid generating device 1 can be installed in the bathroom or applied in cleaning. In this case, the adjust-controlling module 19 (not shown) is disposed on the housing, and the user can directly operate it.

The covering body 15 protrudes from the housing 10 through an opening of the housing 10 for connecting to another pipe. For example, the external surface of the covering body 15 is configured with a screw thread for connecting to a water pipe with an internal screw thread. Of course, the covering body 15 can be connected with another pipe by different ways. For example, the covering body 15 has an internal screw thread for connecting to a water pipe with an external screw thread.

In addition, the water inlet of the hydroelectric generator 16 can also be configured with a screw thread for connecting to another pipe.

Moreover, since the covering body 15 is protruded from the opening of the housing 10, the user can easily remove the covering body 15 so as to install the flow limiting unit 13 and the position limiting member 14 into the tube 11 or uninstall them from the tube 11.

The plasma liquid generating device 1 further includes a plurality of plasma generating modules 12. The tube 11 has a plurality of air inlets 111, and the plasma generating modules 12 are disposed corresponding to the air inlets 111.

Figure 9:
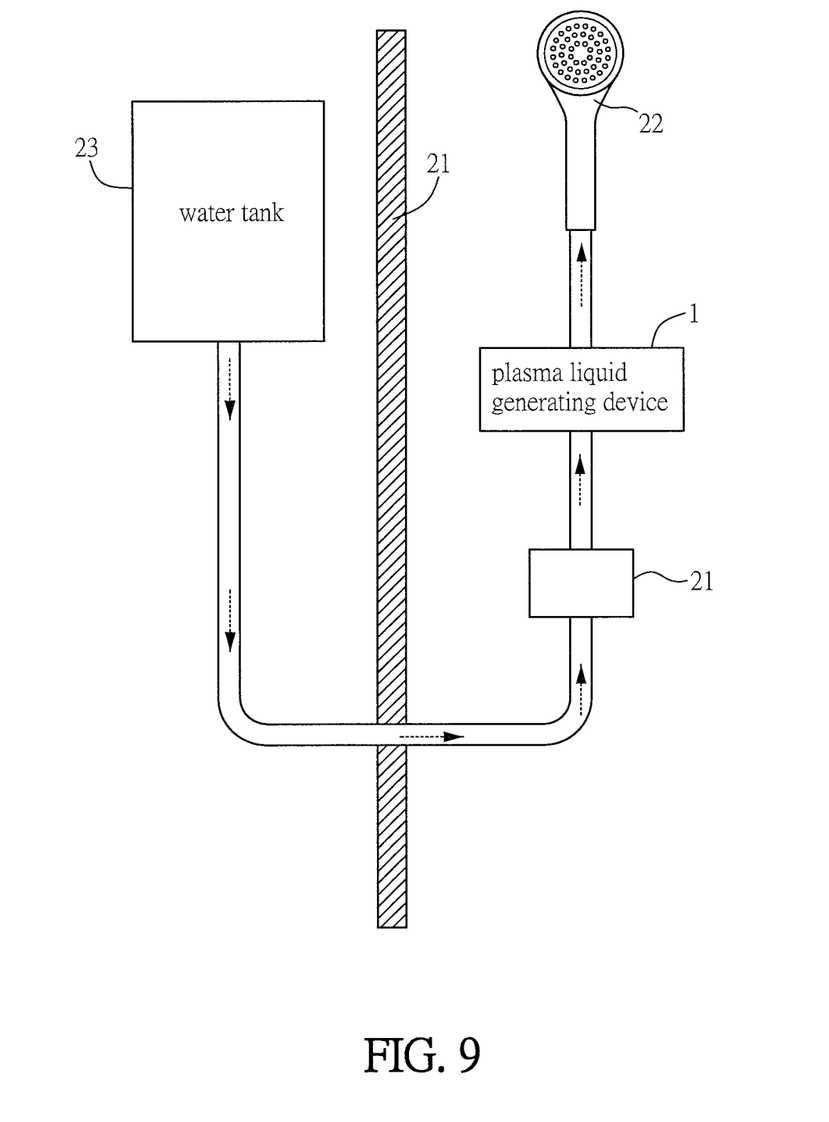
FIGS. 9 and 10 are schematic diagrams showing applications of the plasma liquid generating device.
Figure 10:
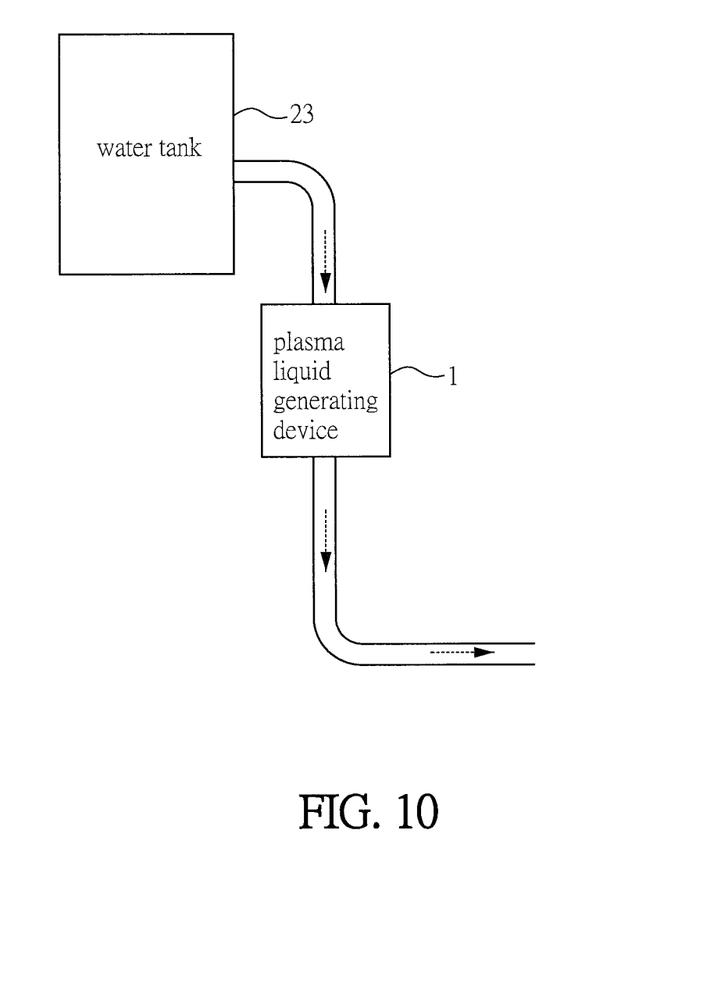

FIGS. 9 and 10 are schematic diagrams showing applications of the plasma liquid generating device.

As shown in FIG. 9, in one embodiment, a pipe connecting the plasma liquid generating device 1 and the water tank 23 may pass through the wall 21. Thus, the plasma liquid generating device 1 can be installed at indoor (e.g. in the bathroom). The water tank 23 can provide water to the plasma liquid generating device 1. A water output structure 22 is connected to the plasma liquid generating device 1, so that the plasma liquid generated by the plasma liquid generating device 1 can be ejected through the water output structure 22 for showering or washing. Herein, the water output structure 22 is for example a microbubble shower, which can eject bubbles of 20 μm. In practice, the microbubble shower can achieve the deep cleaning of skin and thus enhance the cosmetic and sterilization effects of the plasma liquid.

As shown in FIG. 10, the plasma liquid generating device 1 can be installed on the outlet of the water tank 23, and the output pipe of the plasma liquid generating device 1 can be disposed at any desired place. For example, if the house has three bathrooms, the output pipes can be installed to supply the plasma liquid containing the first type plasma particles ($O_3$) and the second type plasma particles ($NO_3^-$) to the three bathrooms.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A plasma liquid generating device, comprising:
   a tube having at least an air inlet and a flow channel outlet;
   a plasma generating module disposed adjacent to the air inlet and configured to generate plasma;
   a flow limiting unit detachably disposed in the tube, wherein a distance between the flow limiting unit and the flow channel outlet is greater than a distance between the air inlet and the flow channel outlet; and
   a position limiting member detachably disposed at the flow channel outlet to limit a position of the flow limiting unit.

2. The plasma liquid generating device of claim 1, wherein the plasma generating module ionizes air outside the tube to form the plasma, a water flow passes through the flow limiting unit so as to suck the plasma into the tube through the air inlet, and the plasma is then mixed in the water flow.

3. The plasma liquid generating device of claim 1, wherein the flow limiting unit has a ball shape, and a surface of the flow limiting unit contains soluble minerals.

4. The plasma liquid generating device of claim 1, wherein the flow limiting unit comprises:
   a core part comprising a non-water soluble material; and
   a functional coating part comprising a water soluble material and covering the core part.

5. The plasma liquid generating device of claim 4, wherein the functional coating part comprises:
   a functional surface layer comprising soluble minerals; and
   a deep layer disposed between the core part and the functional surface layer and having a water soluble property different from the functional surface layer.

6. The plasma liquid generating device of claim 1, wherein the flow channel outlet of the tube is large enough for configuring the flow limiting unit.

7. The plasma liquid generating device of claim 1, further comprising:
   a covering body disposed at one end of the tube;
   wherein the position limiting member is disposed on the covering body and extends toward an inside part of the tube; and
   when the flow limiting unit is pushed by a water flow, the position limiting member stops the flow limiting unit to prevent the water flow to carry the flow limiting unit toward the flow channel outlet.

8. The plasma liquid generating device of claim 1, wherein the position limiting member comprises:
   a ring body having one side matching the flow channel outlet; and
   at least a position limiting stick extending from the ring body toward an inside part of the tube;
   wherein when a water flow pushes the flow limiting unit, the position limiting stick stops the flow limiting unit to prevent the water flow to carry the flow limiting unit.

9. The plasma liquid generating device of claim 1, further comprising:
   a driving circuit coupled with the plasma generating module and driving the plasma generating module to generate first type plasma particles and second type plasma particles; and
   an adjust-controlling unit coupled with the driving circuit and controlling the driving circuit to control a generation proportion of the first type plasma particles and the second type plasma particles generated by the plasma generating module;
   wherein the first type plasma particles are ozone, the second type plasma particles are nitrate ions, the driving circuit outputs a driving voltage to the plasma generating module;
   when the driving voltage has a high frequency, the generated nitrate ions are more than the generated ozone in the generation proportion; and
   when the driving voltage has a low frequency, the generated ozone is more than the generated nitrate ions in the generation proportion.

10. The plasma liquid generating device of claim 1, further comprising:
    a hydroelectric generator for providing power to the plasma generating module; and
    a waterproof housing for accommodating the tube, the plasma generating module, the flow limiting unit, the position limiting member, and the hydroelectric generator.

11. A plasma liquid generating device, comprising:
    a tube having at least an air inlet and a flow channel outlet;
    a plasma generating module disposed adjacent to the air inlet and configured to ionize air outside the tube to form plasma;
    a flow limiting unit detachably disposed in the tube, wherein a distance between the flow limiting unit and the flow channel outlet is greater than a distance between the air inlet and the flow channel outlet, a water flow passes through the flow limiting unit so as to suck the plasma into the tube through the air inlet, the plasma is then mixed in the water flow, and the flow channel outlet of the tube is large enough for configuring the flow limiting unit;

a position limiting member detachably disposed at the flow channel outlet to limit a position of the flow limiting unit;

a hydroelectric generator for providing power to the plasma generating module;

a driving circuit coupled with the plasma generating module and driving the plasma generating module to generate ozone and nitrate ions;

a waterproof housing for accommodating the tube, the plasma generating module, the flow limiting unit, the position limiting member, the driving circuit, and the hydroelectric generator; and an adjust-controlling unit coupled with the driving circuit and controlling the driving circuit to control a generation proportion of the ozone and the nitrate ions generated by the plasma generating module;

wherein the driving circuit outputs a driving voltage to the plasma generating module;

when the driving voltage has a high frequency, the generated nitrate ions are more than the generated ozone in the generation proportion; and when the driving voltage has a low frequency, the generated ozone is more than the generated nitrate ions in the generation proportion.

12. The plasma liquid generating device of claim 11, wherein the flow limiting unit has a ball shape, and a surface of the flow limiting unit contains soluble minerals.

13. The plasma liquid generating device of claim 12, wherein the flow limiting unit comprises:

a core part comprising a non-water soluble material; and a functional coating part comprising a water soluble material and covering the core part.

14. The plasma liquid generating device of claim 13, wherein the functional coating part comprises:

a functional surface layer comprising soluble minerals; and a deep layer disposed between the core part and the functional surface layer and having a water soluble property different from the functional surface layer.

15. The plasma liquid generating device of claim 11, further comprising:

a covering body disposed at one end of the tube;

wherein the position limiting member is disposed on the covering body and extends toward an inside part of the tube; and when the flow limiting unit is pushed by the water flow, the position limiting member stops the flow limiting unit to prevent the water flow to carry the flow limiting unit toward the flow channel outlet.

16. The plasma liquid generating device of claim 11, wherein the position limiting member comprises:

a ring body having one side matching the flow channel outlet; and at least a position limiting stick extending from the ring body toward an inside part of the tube;

wherein when the water flow pushes the flow limiting unit, the position limiting stick stops the flow limiting unit to prevent the water flow to carry the flow limiting unit.

* * * * *